(12) United States Patent
Hawkins (10) Patent No.: US 9,138,221 B2
(45) Date of Patent: Sep. 22, 2015

(54) ANTI-BACKUP SUTURE ANCHOR

(71) Applicant: J. Riley Hawkins, Cumberland, RI (US)

(72) Inventor: J. Riley Hawkins, Cumberland, RI (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 410 days.

(21) Appl. No.: 13/623,258

(22) Filed: Sep. 20, 2012

(65) Prior Publication Data

US 2014/0081323 A1    Mar. 20, 2014

(51) Int. Cl.
*A61B 17/04* (2006.01)

(52) U.S. Cl.
CPC ..... *A61B 17/0401* (2013.01); *A61B 2017/0427* (2013.01); *A61B 2017/0445* (2013.01); *A61B 2017/0448* (2013.01); *A61B 2017/0451* (2013.01)

(58) Field of Classification Search
CPC ............... A61B 17/0401; A61B 2017/0427; A61B 2017/0448; A61B 2017/0451; A61B 2017/0445
See application file for complete search history.

(56) References Cited

U.S. PATENT DOCUMENTS

| | | | |
|---|---|---|---|
| 5,702,215 A * | 12/1997 | Li | ................................. 411/21 |
| 6,986,781 B2 | 1/2006 | Smith | |
| 7,056,333 B2 | 6/2006 | Walshe | |
| 8,137,381 B2 * | 3/2012 | Foerster et al. | ............... 606/232 |
| 2004/0098050 A1 * | 5/2004 | Foerster et al. | ............... 606/232 |
| 2005/0055052 A1 * | 3/2005 | Lombardo et al. | ............ 606/232 |
| 2006/0282083 A1 * | 12/2006 | Fanton et al. | .................. 606/72 |
| 2007/0276437 A1 * | 11/2007 | Call et al. | ..................... 606/232 |

* cited by examiner

*Primary Examiner* — Gregory Anderson
*Assistant Examiner* — Son Dang (57) ABSTRACT

Devices and methods are provided herein that generally involve suture anchors having one or more anti-backup features configured to resist or prevent backward movement of a suture that is pulled through the suture anchor. In some embodiments, the suture anchor can be configured to permit a suture to slide freely in one direction but resist or prevent suture movement in the opposite direction. For example, cleats can be rotatably mounted within the suture anchor, can project radially outward from an exterior sidewall of the suture anchor, or can project circumferentially from sidewalls of one or more channels formed in the suture anchor's exterior surface.

15 Claims, 7 Drawing Sheets

ANTI-BACKUP SUTURE ANCHOR

FIELD

The present invention relates generally to devices and methods for anchoring sutures in bone or other bodily tissue.

BACKGROUND

Soft tissues, such as ligaments, tendons, and muscles, are attached to a large portion of the human skeleton. In particular, many ligaments and tendons are attached to the bones which form joints, such as shoulder and knee joints. A variety of injuries and conditions require attachment or reattachment of soft tissue to bone. For example, when otherwise healthy tissue has been torn away from a bone, surgery is often required to reattach the tissue to the bone to allow healing and natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures can be preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Proper attachment of soft tissue requires that it be placed in the anatomically correct position to promote optimal healing. Conventional methods for attaching soft tissue to bone have typically used anchors through which sutures can be pulled to draw a piece of soft tissue attached to the suture into proximity of the bone surface after the anchor is inserted in a pre-drilled bone cavity. Such methods then require the free end or ends of the suture to be tied off to hold the soft tissue in place. This requires a high degree of dexterity from the surgeon, and it can be difficult or impossible to maintain ideal tension on the suture while tying the knot, as there is a tendency for the suture to slip.

There is thus a need for improved devices and methods for attaching soft tissue to bone which reduce the tendency for the suture or anchor to pull out of the bone and which allow the suture to be tensioned without slipping and without requiring knot tying.

SUMMARY

Devices and methods are provided herein that generally involve suture anchors having one or more anti-backup features configured to resist or prevent backward movement of a suture that is pulled through the suture anchor. In some embodiments, the suture anchor can be configured to permit a suture to slide freely in one direction but resist or prevent suture movement in the opposite direction. For example, cleats can be rotatably mounted within the suture anchor, can project radially outward from an exterior sidewall of the suture anchor, or can project circumferentially from sidewalls of one or more channels formed in the suture anchor's exterior surface.

In one aspect, a suture anchor is provided that can include an elongate body having proximal and distal ends, an inner cavity formed therein, and first and second elongate cut-outs formed in opposed sides of the elongate body. The suture anchor can also include a suture-engaging element disposed within the inner cavity of the elongate body and having a width that is greater than an outer diameter of the elongate body such that opposed terminal ends of the suture-engaging element protrude radially outward through the first and second elongate cut-outs formed in the elongate body. The suture-engaging element can be configured to allow a suture extending around the elongate body and along the cut-outs to slide freely in a first direction, and to engage the suture and prevent sliding movement of the suture in a second, opposite direction.

The suture-engaging element can be retained within the inner cavity of the elongate body. The suture-engaging element can be at least one of rotatable about a fixed axis within the inner cavity of the elongate body and flexible about a fixed axis within the inner cavity of the elongate body. A first terminal end of the suture-engaging element can be angled proximally toward the proximal end of the elongate body, and a second terminal end of the suture-engaging element can be angled distally toward the distal end of the elongate body. The elongate body can be substantially cylindrical. The elongate body can include one or more bone-engaging features formed on an exterior surface thereof. The suture-engaging element can include a central body portion having first and second arms extending tangentially therefrom in opposite directions. The terminal ends of the first and second arms can include channels configured to receive a suture therein, the channels being defined between sharp tips configured to engage bone. The suture-engaging element can include a central body portion having first and second arms extending therefrom, the first and second arms having respective first and second elbows formed therein. When the suture anchor is implanted in a bone, tension applied to the suture in the second, opposite direction can be effective to force the suture-engaging element into engagement with the bone.

In another aspect, a suture anchor is provided that can include an elongate body having proximal and distal ends and a plurality of surface features formed on an external surface of the elongate body for engaging bone. The suture anchor can also include first and second series of cleats aligned longitudinally along first and second opposite sides of the elongate body, the first series of cleats being angled proximally toward the proximal end of the elongate body and the second series of cleats being angled distally toward the distal end of the elongate body.

The first series of cleats can be configured to prevent a suture from sliding distally relative thereto while allowing a suture to freely slide proximally relative thereto, and the second series of cleats can be configured to prevent a suture from sliding proximally thereto while allowing a suture to freely slide distally relative thereto. When the suture anchor is implanted in a bone, tension applied to a suture in a first direction can be effective to force the first and second series of cleats into engagement with the bone and tension applied to the suture in a second, opposite direction can be effective to pull the first and second series of cleats out of engagement with the bone. The suture anchor can include a suture-receiving member formed in a distal end of the elongate body for receiving a suture therethrough. The elongate body and the first and second series of cleats can comprise a unitary member, or the first and second series of cleats can be formed as separate inserts and can be attached to the elongate body.

In another aspect, a method for anchoring tissue to bone is provided that can include inserting a suture anchor into bone and applying tension to free ends of a suture coupled to the suture anchor such that the suture slides around the suture anchor and pulls soft tissue coupled to a looped end of the suture toward the suture anchor. The suture anchor can include at least one suture-engaging element that allows the suture to slide in a first direction relative to the suture anchor, but that engages and prevents the suture from sliding in a second opposite direction relative to the suture anchor to thereby lock the suture relative to the suture anchor and thereby secure the soft tissue to the bone.

The suture-engaging element can include a rotating cleat having opposed terminal ends that extend radially outward from opposed sides of the suture anchor, wherein the rotating cleat rotates to engage and prevent movement of the suture in the second direction. The suture-engaging element can include first and second series of cleats formed on an external surface of the suture anchor and extending longitudinally therealong, the first series of cleats being angled proximally to prevent the suture from sliding distally relative thereto, and the second series of cleats being angled distally to prevent the suture from sliding proximally relative thereto. The method can also include forcing the suture-engaging element into engagement with the bone by releasing tension from the free ends of the suture and allowing the soft tissue to exert a pulling force on the suture in the second opposite direction.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Devices and methods are provided herein that generally involve suture anchors having one or more anti-backup features configured to resist or prevent backward movement of a suture that is pulled through the suture anchor. In some embodiments, the suture anchor can be configured to permit a suture to slide freely in one direction but resist or prevent suture movement in the opposite direction. For example, cleats can be rotatably mounted within the suture anchor, can project radially outward from an exterior sidewall of the suture anchor, or can project circumferentially from sidewalls of one or more channels formed in the suture anchor's exterior surface.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
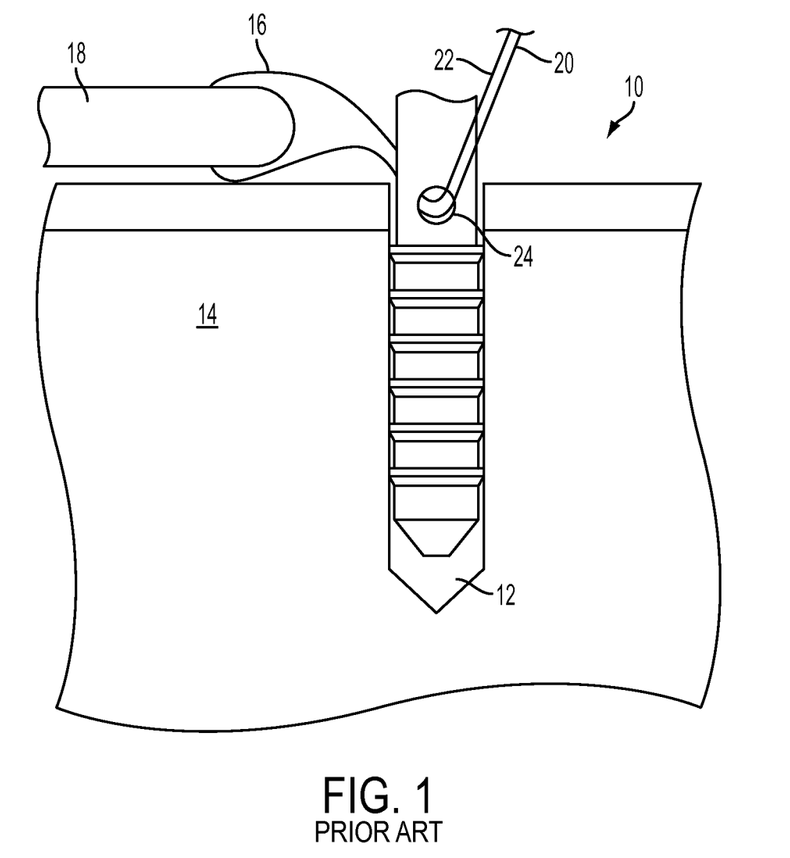
FIG. 1 is a cross-sectional side view of a bone with soft tissue approximated thereto using a prior art suture anchor.

FIG. 1 illustrates a prior art suture anchor 10. In use, the suture anchor 10 is inserted into a bore hole 12 formed in a bone 14. A length of suture 16 is threaded through a piece of soft tissue 18 and the two free ends 20, 22 of the suture 16 are passed through an aperture 24 in the suture anchor 10. Tension is applied to the two free ends 20, 22 of the suture 16 to approximate the soft tissue 18 to the bone 14. The two free ends 20, 22 of the suture 16 are then tied together in a knot (not shown) to hold the soft tissue 18 in place adjacent to the bone 14. As noted above, it can be difficult and time consuming to tie the suture ends 20, 22 in a knot, particularly during minimally-invasive procedures. In addition, the suture 16 tends to slip during the knot-tying operation or after the surgery is completed, making it difficult to maintain the soft tissue 18 in close approximation to the bone 14 and under appropriate tension.

Figure 2:
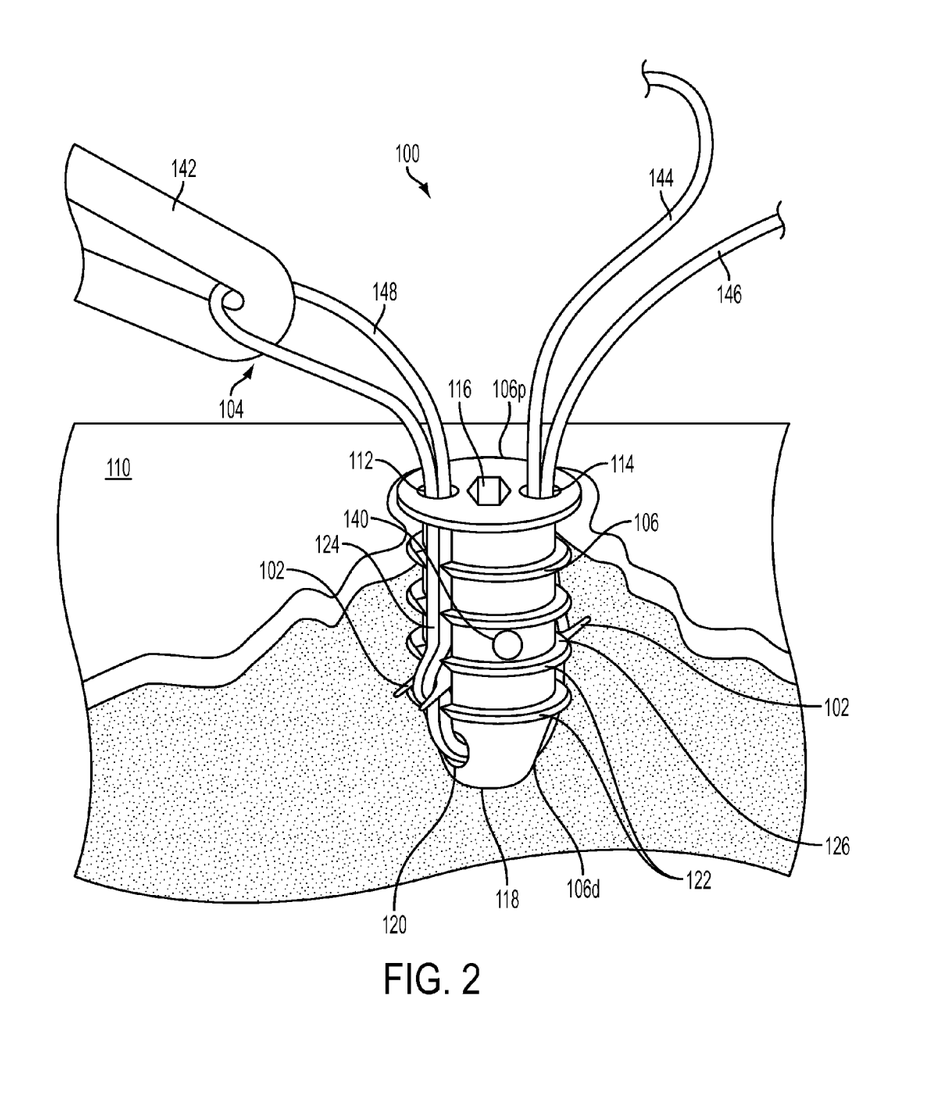
FIG. 2 is a cross-sectional perspective view of a bone with an exemplary embodiment of a suture anchor implanted therein, the suture anchor having a rotating suture-engaging element.
Figure 3:
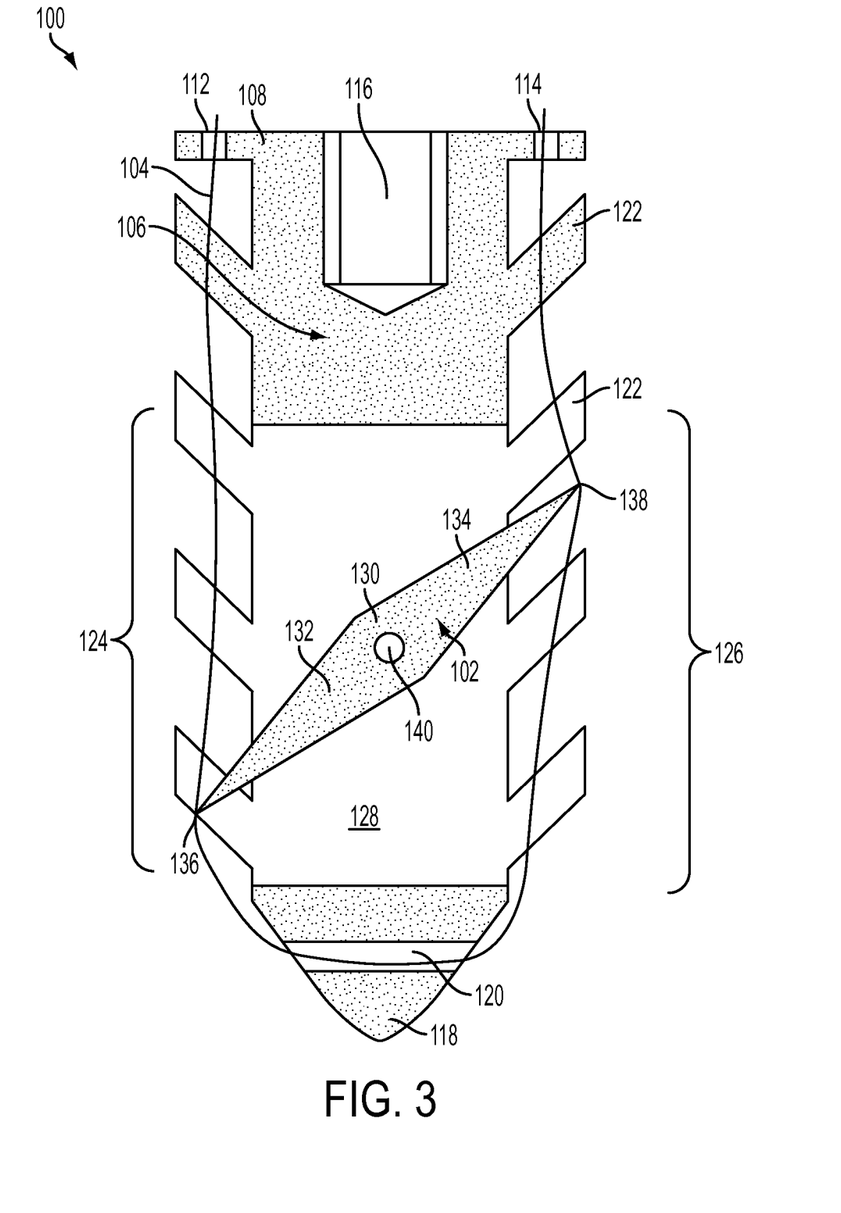
FIG. 3 is a cross-sectional side view of the suture anchor of FIG. 2.

FIGS. 2 and 3 illustrate an exemplary embodiment of a suture anchor 100 that includes a suture-engaging element 102 for resisting or preventing suture backup. In particular, the suture-engaging element 102 can permit a suture 104 to be pulled tightly in a first direction and can prevent the suture 104 from sliding in a second, opposite direction.

The illustrated suture anchor 100 is generally in the form of an elongate body 106 having proximal and distal ends 106p, 106d. While a substantially-cylindrical elongate body 106 is shown, the elongate body can also have other shapes, including that of a rectangle or that of a cone that tapers from a larger-diameter proximal end to a smaller-diameter distal end.

A head 108 is formed at the proximal end 106p of the elongate body 106. In some embodiments, the head 108 can be a substantially planar radial flange and can be configured to lie flush or sub-flush with the surface of a bone 110 in which the suture anchor 100 is implanted. The suture anchor can alternatively be headless. The head 108 can also include first and second proximal apertures 112, 114 through which the suture 104 can be received. In some embodiments, the proximal apertures 112, 114 can have a diameter that is at least twice the diameter of the suture 104 to be secured using the anchor, such that two lengths of the suture 104 can pass through each aperture 112, 114 at the same time. The head 108 can also include any of a variety of driving interfaces, such as a hexagonal recess 116.

The distal end 106d of the elongate body 106 can include a pointed or rounded tip 118 to facilitate insertion into a bone opening. The distal end 106d of the elongate body 106 can also include a distal aperture 120 through which the suture 104 can be received. The distal aperture 120 can extend through the elongate body 106, transverse to the planes in which the first and second cut-outs 124, 126 lie. Like the proximal apertures 112, 114 discussed above, the distal aperture 120 can have a diameter that is at least twice that of the suture 104 to be secured using the anchor, such that two lengths of the suture 104 can pass through the aperture 120 at the same time. While a distal aperture 120 is shown and described herein, various other suture-receiving members can be used instead or in addition, such as an open-ended slot.

The exterior surface of the elongate body 106 can include one or more bone-engaging features 122 formed thereon, such as a helical thread or a plurality of annular projections. When the anchor 100 is threaded or press-fit into the bone opening, such features 122 can resist or prevent the anchor 100 from being pulled out of the bone opening in the proximal direction. The exterior surface of the elongate body 106 can also include first and second elongate cut-outs 124, 126 through which portions of the suture-engaging element 102 can pass, as described below. The elongate cut-outs 124, 126 can also act as reliefs or channels in the exterior sidewall of the suture anchor 100 in which one or more lengths of the suture 104 can be received. In the illustrated embodiment, the first and second elongate cut-outs 124, 126 are formed in diametrically-opposite sides of the suture anchor 100.

An inner cavity or lumen 128 can be formed within the suture anchor 100 for housing the suture-engaging element 102. In the illustrated embodiment, the inner cavity 128 extends laterally through the elongate body 106 and is opened to the surrounding bone 110 via the first and second elongate cut-outs 124, 126. The inner cavity 128 can terminate proximal to the distal aperture 120 or other suture-receiving member provided in the distal end of the suture anchor 100.

As shown in FIG. 3, the suture-engaging element 102 can extend across the inner cavity 128 and protrude through the first and second elongate cut-outs 124, 126 to interact with a suture 104. The suture-engaging element 102 can be configured to allow the suture 104 to be pulled in a first direction through the suture anchor 100 and to resist or prevent the suture from being pulled in a second opposite direction through the suture anchor. The suture-engaging element 102 includes a central body portion 130 with first and second arms 132, 134 extending laterally therefrom. The arms can be contoured or tapered such that they converge to pointed terminal ends 136, 138. The suture-engaging element 102 can be rotatably mounted within the inner cavity 128 of the suture anchor 100. For example, a cross pin 140 can extend through an axial opening formed in the central body portion 130 of the suture-engaging element 102 and can extend laterally through the elongate body 106 of the suture anchor 100, perpendicular to a plane in which the first and second elongate cut-outs 124, 126 lie. The suture-engaging element 102 can thus be rotatable about a fixed axis within the cavity 128. In some embodiments, the suture-engaging element 102 can be flexible about a fixed axis within the cavity 128, such that the suture-engaging element 102 is configured to bend or deflect into engagement or into greater engagement with a suture when the suture is pulled in a first direction, and to bend or deflect out of engagement or into lesser engagement with the suture when the suture is pulled in a second, opposite direction. In such embodiments, the suture-engaging element 102 can be rotatably or non-rotatably mounted within the cavity 128. The suture-engaging element 102 can optionally be molded into the cavity 128, such that it is formed integrally with the elongate body 106. The extent to which the suture-engaging element 102 is permitted to rotate or flex can be limited in some embodiments by the dimensions of the cavity 128. The suture-engaging element 102 can be mounted such that the first arm 134 is angled proximally toward the proximal end of the suture anchor 100 and the second arm 132 is angled distally toward the distal end of the suture anchor 100.

The suture-engaging element 102 can have a width that is greater than the outer diameter of the elongate body 106, such that the opposed terminal ends 136, 138 of the suture-engaging element 102 can protrude radially outward from the elongate body 106 through the first and second cut-outs 124, 126 and into contact with surrounding bone. The width of the suture-engaging element 102 can also be greater than the diameter of the bone-engaging features 122 formed on the exterior of the elongate body 106. In some embodiments, the width of the suture-engaging element 102 can be less than the length of the elongate cut-outs 124, 126, such that the suture-engaging element 102 is prevented from rotating 360 degrees about the cross pin 140.

In use, an incision can be formed in proximity to an area of bone 110 to which a piece of soft tissue 142 is to be approximated. The suture anchor 100 can then be passed through the incision, for example via a minimally-invasive surgical access device, and implanted in the bone 110. A bore-hole can be drilled in the bone 110 and the suture anchor 100 can be threaded or press-fit therein, or the suture anchor 100 can be self-drilled or self-tapped directly into unprepared bone 110.

The suture anchor 100 can be pre-loaded with the suture 104 before the suture anchor 100 is implanted in bone. Alternatively, the suture 104 can be threaded through the anchor 100 after implantation, for example using a common shuttle maneuver. In either case, as shown in FIG. 2, the two free ends 144, 146 of a length of suture 104 can be brought together such that the suture forms an open loop 148. Soft tissue 142 can be captured in the looped portion 148 of the suture 104 as shown, or the suture 104 can be threaded through the soft tissue 142, e.g., using a suture needle. The two free ends 144, 146 of the suture 104 can be threaded through the first proximal aperture 112 in the head 108 of the suture anchor 100, down along the length of the suture anchor through the first elongate cut-out 124, through the distal aperture 120, back up along the length of the suture anchor through the second elongate cut-out 126, and through the second proximal aperture 114 in the head 108. Exemplary techniques for loading a suture anchor with a suture are disclosed in U.S. application Ser. No. 13/623,290, entitled SUTURE LEADER, and filed on Sep. 20, 2012, the entire contents of which are incorporated herein by reference. Further exemplary techniques are disclosed in U.S. application Ser. No. 13/623,467, entitled SUTURE WITH VARIABLE PICK COUNT, and filed on Sep. 20, 2012, the entire contents of which are incorporated herein by reference.

Once the suture anchor 100 is implanted in bone and the suture 104 is threaded therethrough, the surgeon can apply tension to the two free ends 144, 146 of the suture. This can cause the suture-engaging element 102 to rotate counter-clockwise in the illustrated embodiment, such that the opposed terminal ends 136, 138 thereof move out of engagement with the surrounding bone opening and the suture 104 is free to slide past the suture-engaging element 102. As the free ends 144, 146 of the suture are pulled, the suture 104 slides counterclockwise through the suture anchor 100, drawing the piece of soft tissue 142 at the looped end 148 of the suture 104 into approximation with the bone surface 110. In particular, the portion of the suture in the first elongate cut-out 124 slides distally while the portion of the suture in the second elongate cut-out 126 slides proximally. When tension is released from the two free ends 144, 146 of the suture 104, the natural tension of the soft tissue 142 applies a pulling force to the suture in a clockwise direction. This can cause the suture-engaging element 102 to rotate clockwise, at which time the opposed terminal ends 136, 138 of the suture-engaging element 102 bite into the surrounding bone and pinch down on the suture 104. The force applied to the suture 104 resists or prevents the suture from slipping in the clockwise direction.

It will thus be appreciated that the soft tissue 142 can be quickly and easily approximated to the bone surface 110, without the need to ever tie off the two free ends 144, 146 of the suture 104 in a knot. After the soft tissue 142 is approximated as desired, the two free ends 144, 146 of the suture 104 can be trimmed and the incision can be closed. It will be further appreciated that tension applied in the clockwise direction by the soft tissue 142 only causes the suture anchor 100 to become more secure in the bone opening, as such tension forces the suture-engaging element 102 more firmly into engagement with the surrounding bone 110. The suture anchor 100 thus permits the suture anti-backup and anchor retention functions to be combined in a single feature of the device. In some embodiments, the two free ends 144, 146 of the suture can be tied off or secured using a knotting element.

Figure 4:
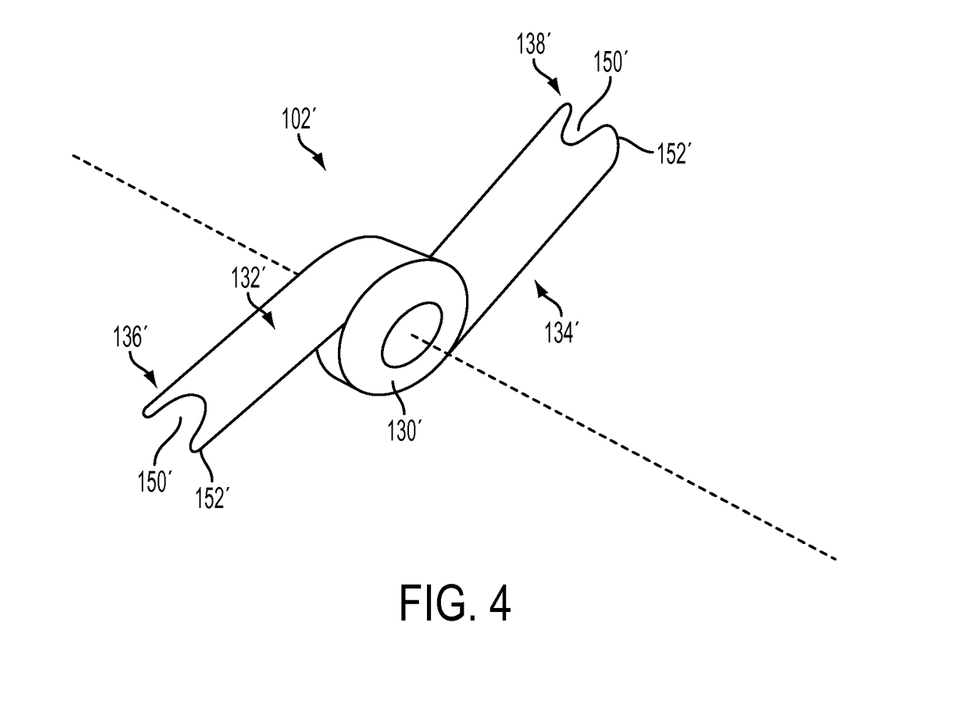
FIG. 4 is a perspective view of another exemplary embodiment of a suture-engaging element.

FIG. 4 illustrates another exemplary embodiment of a suture-engaging element 102'. As shown, the element 102' includes a central body portion 130' with first and second arms 132', 134' extending tangentially therefrom in opposite directions. The central body portion 130' can be cylindrical and can include an axial opening for receiving the cross pin 140 described above. The opposed-terminal ends 136', 138' of the first and second arms 132', 134' can include U-shaped channels 150' defined between sharp tips 152' configured to cut or bite into surrounding bone. The dimensions of the U-shaped channels 150' can be selected based on the size of the suture to be anchored using the suture anchor. In some embodiments, the U-shaped channels 150' have an area that is less than twice the cross-sectional area of the suture, such that two lengths of suture extending through the U-shaped channel 150' are pinched when the suture-engaging element 102' is driven against adjacent bone. Any of the other suture-engaging elements disclosed herein can also include similar U-shaped channels. The suture-engaging element can also have other tip configurations, such as a single point, a plurality of teeth, and so forth. The channels can alternatively be V-shaped, flat-bottomed U-shaped, or a shape that matches or is slightly smaller than the suture cross section.

Figure 5:
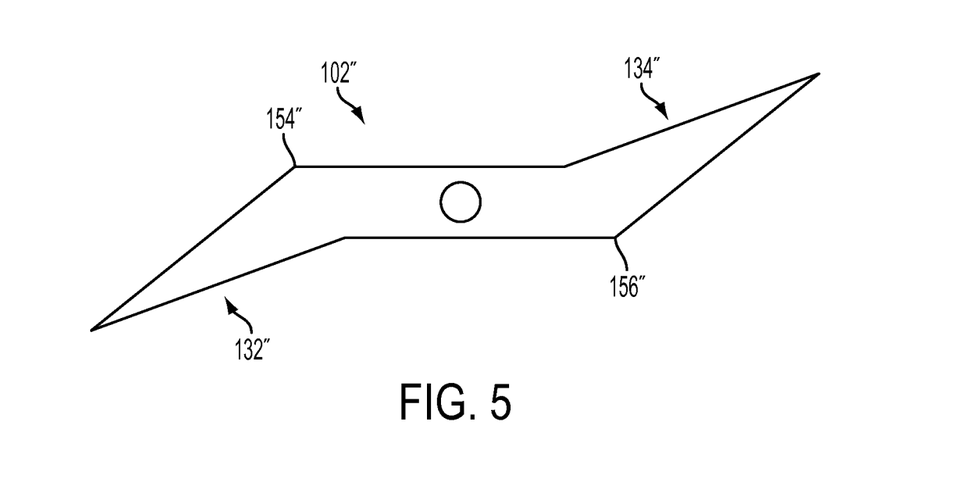
FIG. 5 is a side view of another exemplary embodiment of a suture-engaging element.

FIG. 5 illustrates another exemplary embodiment of a suture-engaging element 102", in which the first and second arms 132", 134" include respective first and second elbows 154", 156" formed therein. Each arm 132", 134" includes a first portion having parallel sidewalls and a second portion having angled or tapered sidewalls. In other words, the suture-engaging element 102" includes a linear central portion, and two tips that extend at an angle relative to the central portion and that are angled in opposite directions relative to one another.

While a single suture-engaging element 102 is shown in the illustrated suture anchor 100, it will be appreciated that the suture anchor can also include more than one suture-engaging element. For example, a plurality of suture engaging elements can be disposed within the interior cavity 128 of the suture anchor 100. In some embodiments, each of the suture-engaging elements can be rotatable about axes that are parallel to one another and each of the suture-engaging elements can pass through the first and second elongate-cut-outs 124, 126 to engage the same suture. In other embodiments, one or more suture-engaging elements can be rotatable about an axis or axes which are perpendicular to the axis or axes about which one or more other suture-engaging elements rotate. In such embodiments, third and fourth longitudinal cut-outs can be formed in the elongate body 106 offset 90 degrees from the first and second longitudinal cut-outs 124, 126, respectively, and a second suture can be threaded through the suture anchor 100 and engaged by the suture-engaging elements.

Figure 6:
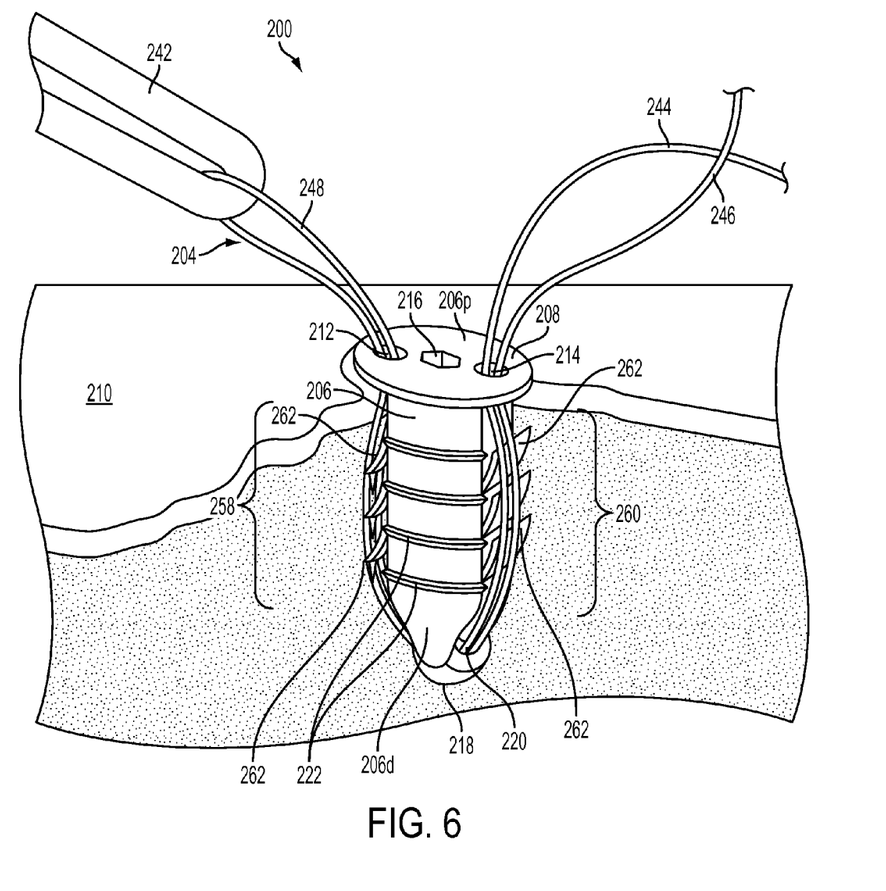
FIG. 6 is a cross-sectional perspective view of a bone with an exemplary embodiment of a suture anchor implanted therein, the suture anchor having first and second series of cleats formed on a sidewall of the suture anchor.

FIG. 6 illustrates an exemplary embodiment of a suture anchor 200 that includes first and second series of cleats 258, 260 formed thereon that can permit a suture 204 to be pulled tightly in a first direction and can prevent the suture from slipping in a second, opposite direction. The series of cleats 258, 260 on the surface of the suture anchor 200 can be provided in place of the first and second elongate cut-outs 124, 126 of the suture anchor 100 described above. The illustrated suture anchor 200 is generally in the form of an elongate body 206 having proximal and distal ends 206p, 206d. While a substantially-cylindrical elongate body 206 is shown, the elongate body 206 can also have other shapes, including that of a rectangle or that of a cone that tapers from a larger-diameter proximal end to a smaller-diameter distal end.

A head 208 is formed at the proximal end 206p of the elongate body 206. In some embodiments, the head 208 can be a substantially planar radial flange and can be configured to lie flush or sub-flush with the surface of a bone 210 in which the suture anchor 200 is implanted. The suture anchor 200 can alternatively be headless. The head 208 can also include first and second proximal apertures 212, 214 through which the suture 204 can be received. In some embodiments, the proximal apertures 212, 214 can have a diameter that is at least twice the diameter of the suture 204 to be secured using the anchor, such that two lengths of the suture 204 can pass through each aperture 212, 214 at the same time. The head 208 can also include any of a variety of driving interfaces, such as a hexagonal recess 216.

The distal end 206d of the elongate body 206 can include a pointed or rounded tip 218 to facilitate insertion into a bone opening. The distal end 206d of the elongate body 206 can also include a distal aperture 220 through which the suture 204 can be received. The distal aperture 220 can extend through the elongate body 206, transverse to the planes in which the first and second series of cleats 258, 260 lie. Like the proximal apertures 212, 214 discussed above, the distal aperture 220 can have a diameter that is at least twice that of the suture 204 to be secured using the anchor, such that two lengths of the suture 204 can pass through the aperture 220 at the same time. While a distal aperture 220 is shown and described herein, various other suture-receiving members can be used instead or in addition, such as an open-ended slot.

The exterior surface of the elongate body 206 can include one or more bone-engaging features 222 formed thereon, such as a helical thread or a plurality of annular projections. When the anchor 200 is threaded or press-fit into the bone opening, such features 224 can resist or prevent the anchor from being pulled out of the bone opening in the proximal direction. The exterior surface of the elongate body 206 can also include first and second series of cleats 258, 260 aligned longitudinally along first and second diametrically-opposite sides of the suture anchor 200. Each series of cleats 258, 260 can include one or more ramped projections 262 extending at an angle from the elongate body 206. The first and second series of cleats 258, 260 can be angled in opposite directions (e.g., the first series of cleats 258 can be angled toward the distal end 206d of the elongate body 206 while the second series of cleats 260 can be angled toward the proximal end 206p of the elongate body 206). In some embodiments, each series of cleats includes at least 3, 4, 5, 6, or 7 or more cleats.

The cleats can be spaced longitudinally along the elongate body 206 and can extend from the elongate body at any of a variety of angles, e.g., less than about 90 degrees, more preferably between about 5 degrees and about 60 degrees, and more preferably between about 10 degrees and about 45 degrees. In some embodiments, the first and second series of cleats 258, 260 can be formed integrally with the elongate body 206, e.g., by injection molding. In other embodiments, the series of cleats 258, 260 can be formed as separate inserts that are attached to the elongate body 206 using adhesion, sonic welding, or other known attachment techniques. The inserts can be formed from the same material as the elongate body 206 or from a different material. The width of the cleats can be selected based on a variety of factors, such as the size of the suture anchor 200 and the size of the suture with which the anchor 200 is to be used. In some embodiments, the cleats extend widthwise across approximately 30 to 90 degrees of the suture anchor's circumference.

In use, an incision can be formed in proximity to an area of bone 210 to which a piece of soft tissue 242 is to be approximated. The suture anchor 200 can then be passed through the incision, for example via a minimally-invasive surgical access device, and implanted in the bone 210. A bore-hole can be drilled in the bone and the suture anchor 200 can be threaded or press-fit therein, or the suture anchor 200 can be self-drilled or self-tapped directly into unprepared bone 210.

The suture anchor 200 can be pre-loaded with a suture 204 before the suture anchor is implanted in bone. Alternatively, the suture 204 can be threaded through the anchor 200 after implantation, for example using a common shuttle maneuver. In either case, as shown in FIG. 6, the two free ends 244, 246 of a length of suture 204 can be brought together such that the suture forms an open loop 248. Soft tissue 242 can be captured in the looped portion 248 of the suture 204 as shown, or the suture can be threaded through the soft tissue, e.g., using a suture needle. The two free ends 244, 246 of the suture 204 can be threaded through the first proximal aperture 212 in the head 208 of the suture anchor 200, down along the first series of cleats 258, through the distal aperture 220, up along the second series of cleats 260, and through the second proximal aperture 214 in the head.

Once the suture anchor 200 is implanted in bone 210 and the suture 240 is threaded therethrough, the surgeon can apply tension to the two free ends 244, 246 of the suture. This can cause the projections 262 of the first and second series of cleats 258, 260 to deflect inwardly towards the elongate body 208 of the suture anchor 200 and out of engagement with surrounding bone, such that the suture 204 is free to slide counterclockwise. In other words, the suture 204 is free to slide distally along the smooth ramped surfaces of the first series of cleats 258 and proximally along the smooth ramped surfaces of the second series of cleats 260. As the free ends 244, 246 of the suture 204 are pulled, the suture slides counterclockwise through the suture anchor 200, drawing the piece of soft tissue 242 at the looped end 248 of the suture into approximation with the bone surface 210. When tension is released from the two free ends 244, 246 of the suture 204, the natural tension of the soft tissue 242 applies a pulling force to the suture in a clockwise direction. This can cause the sharp ends of the projections 262 of the first and second series of cleats 258, 260 to deflect radially-outwards from the elongate body 208 of the suture anchor 200, pinching the suture 204 against the surrounding bone 210 and engaging the bone. The force applied to the suture 204 resists or prevents the suture from slipping in the clockwise direction.

It will thus be appreciated that the soft tissue 242 can be quickly and easily approximated to the bone surface 210, without the need to ever tie off the two free ends 244, 246 of the suture 204 in a knot. After the soft tissue 242 is approximated as desired, the two free ends 244, 246 of the suture 204 can be trimmed and the incision can be closed. It will be further appreciated that tension applied in the clockwise direction by the soft tissue 242 only causes the suture anchor 200 to become more secure in the bone opening, as such tension forces the first and second series of cleats 258, 260 more firmly into engagement with the surrounding bone 210. The suture anchor 200 thus permits the suture anti-backup and anchor retention functions to be combined in a single feature of the device. In some embodiments, the two free ends 244, 246 of the suture can be tied off or secured using a knotting element.

In addition, the positioning of the series of cleats 258, 260 on the exterior of the suture anchor 200 reserves the interior space of the anchor for the driving interface 216 or for additional suture tunnels. The cleats 258, 260 can also be made larger as they are positioned at the exterior periphery of the suture anchor 200 where the available surface area is at a maximum. This can allow for a larger degree of cleat excursion, thereby improving the strength and reliability of the suture anchor 200.

While a single pair of radially-extending cleat sets 258, 260 is shown in the illustrated suture anchor 200, it will be appreciated that the suture anchor can also include multiple such pairs. For example, the suture anchor can also include third and fourth series of cleats formed on the elongate body offset 90 degrees from the first and second series of cleats 258, 260, respectively, and a second suture can be threaded through the suture anchor and engaged by the third and fourth series of cleats.

Figure 7:
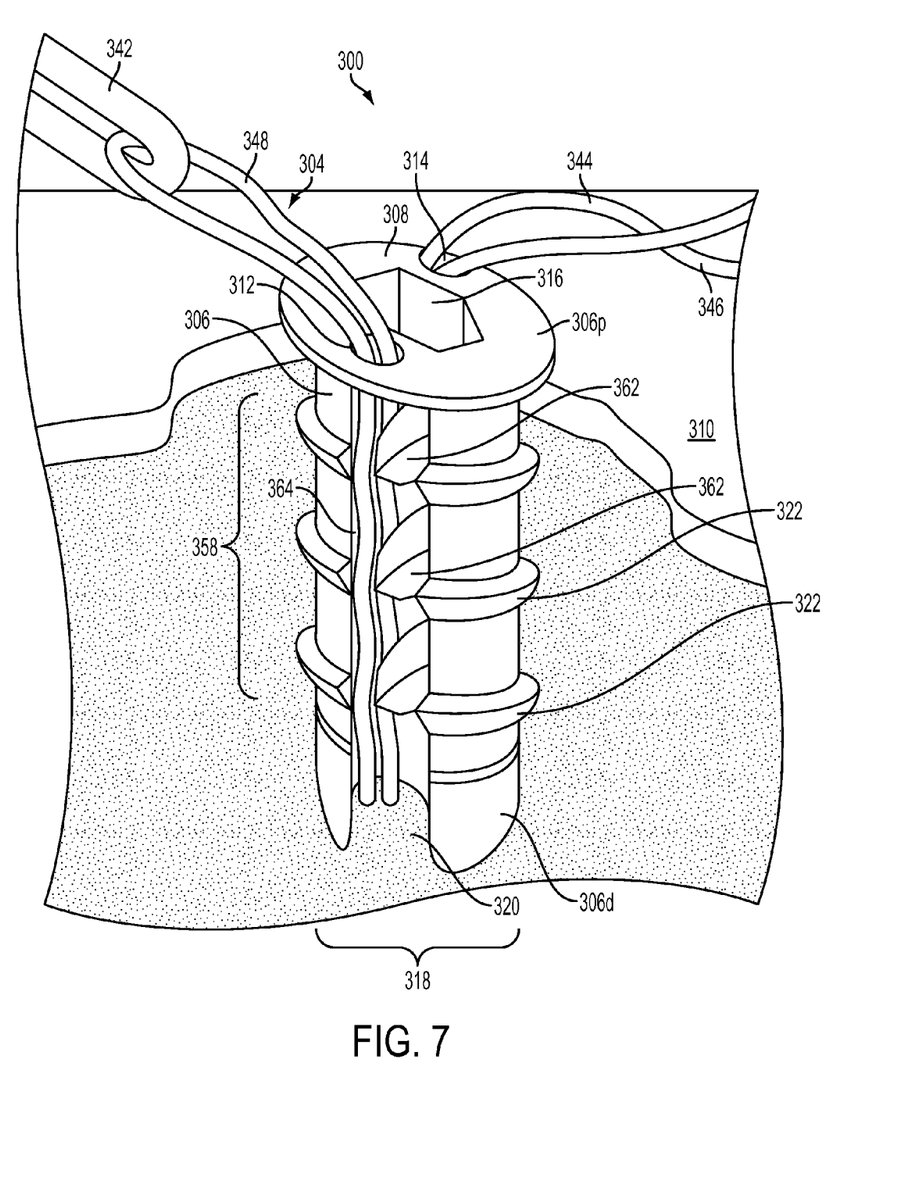
FIG. 7 is a cross-sectional view from a first perspective of a bone with an exemplary embodiment of a suture anchor implanted therein, the suture anchor having first and second series of cleats disposed in channels formed in a sidewall of the suture anchor.
Figure 8:
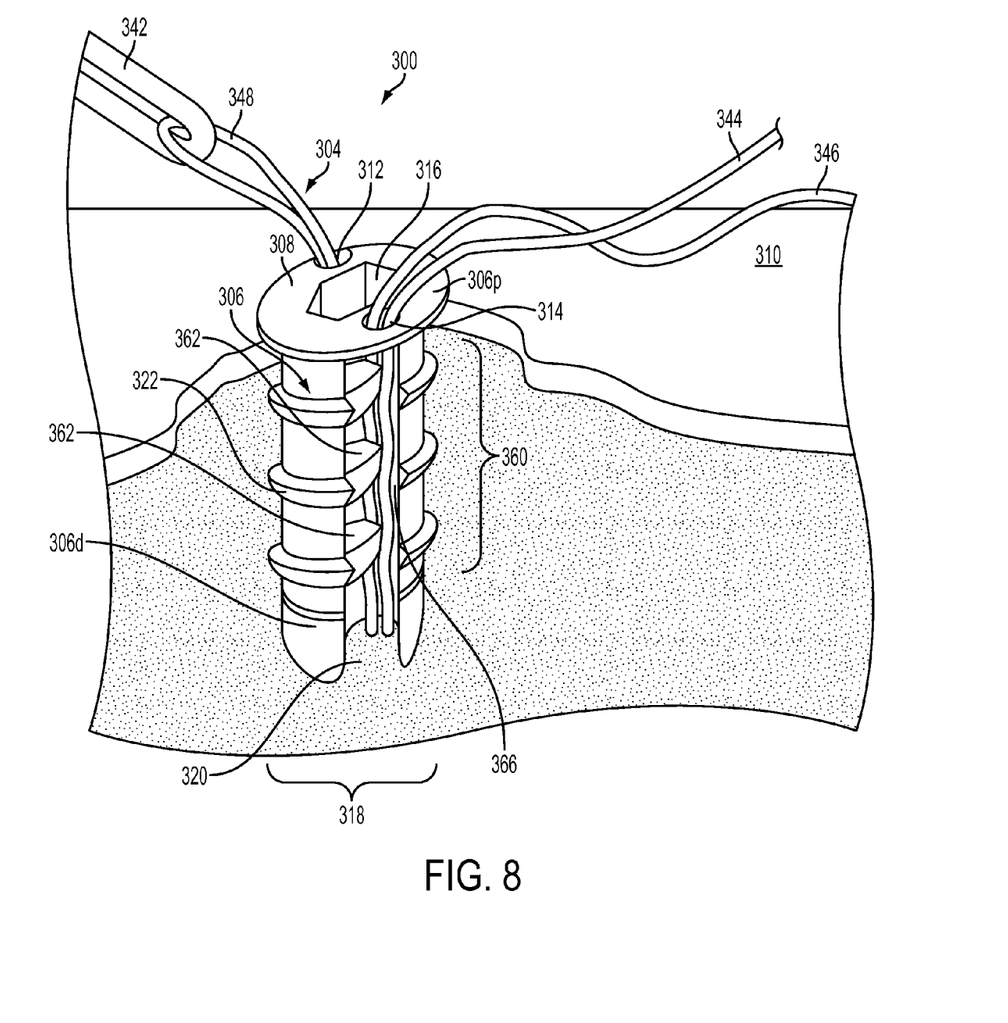
FIG. 8 is a cross-sectional view from a second perspective of the bone and suture anchor of FIG. 7.

FIGS. 7 and 8 illustrate an exemplary embodiment of a suture anchor 300 that includes channels 364, 366 formed in the exterior surface thereof with series of cleats 358, 360 extending circumferentially from sidewalls of the channels. The series of cleats 358, 360 can permit a suture 304 to be pulled tightly in a first direction and can prevent the suture from slipping in a second, opposite direction.

The illustrated suture anchor 300 is generally in the form of an elongate body 306 having proximal and distal ends 306p, 306d. While a substantially-cylindrical elongate body 306 is shown, the elongate body can also have other shapes, including that of a rectangle or that of a cone that tapers from a larger-diameter proximal end to a smaller-diameter distal end.

A head 308 is formed at the proximal end 306p of the elongate body 306. In some embodiments, the head 308 can be a substantially planar radial flange and can be configured to lie flush or sub-flush with the surface of a bone 310 in which the suture anchor 300 is implanted. The suture anchor 300 can alternatively be headless. The head 308 can also include first and second proximal apertures 312, 314 through which the suture 304 can be received. In some embodiments, the proximal apertures 312, 314 can have a diameter that is at least twice the diameter of the suture 304 to be secured using the anchor 300, such that two lengths of the suture 304 can pass through each aperture 312, 314 at the same time. The head 308 can also include any of a variety of driving interfaces, such as a hexagonal recess 316.

The distal end 306d of the elongate body 306 can include a pointed or rounded tip 318 to facilitate insertion into a bone opening. The distal end 306d of the elongate body 306 can also include an open-end slot 320 through which the suture 304 can be received. Alternatively, the distal end 306d of the elongate body 300 can include a distal aperture as shown in the suture anchors 100, 200 described above. The open-end slot 320 can be sized to accommodate two lengths of the suture 304 to be anchored using the suture anchor 300.

The exterior surface of the elongate body 306 can include one or more bone-engaging features 322 formed thereon, such as a helical thread or a plurality of annular projections. When the anchor 300 is threaded or press-fit into the bone opening, such features 322 can resist or prevent the anchor from being pulled out of the bone opening in the proximal direction. The exterior surface of the elongate body 306 can also include first and second elongate reliefs or channels 364, 366 in which one or more lengths of the suture 304 can be received. In the illustrated embodiment, the first and second elongate channels 364, 366 are formed in diametrically-opposite sides of the suture anchor 300.

First and second series of cleats 358, 360 can be disposed longitudinally within the first and second channels 364, 366, respectively. Each series of cleats can include one or more ramped projections 362 extending at an angle from the channel sidewall, such that the cleats extend circumferentially relative to the elongate body 306. The first and second series of cleats 358, 360 can be angled in opposite directions (e.g., the first series of cleats 358 can be angled toward the distal end 306d of the elongate body 306 while the second series of cleats 360 can be angled toward the proximal end 306p of the elongate body 306). In some embodiments, each series of cleats includes at least 3, 4, 5, 6, or 7 or more cleats. The cleats can extend from one sidewall of the channel towards the opposing sidewall of the channel at any of a variety of angles, e.g., less than about 90 degrees, between about 5 degrees and about 60 degrees, and between about 10 degrees and about 45 degrees. In some embodiments, the first and second series of cleats 358, 360 can be formed integrally with the elongate body 306, e.g., by injection molding. In other embodiments, the series of cleats 358, 360 can be formed as separate inserts and attached to the elongate body 306 using adhesion, sonic welding, or other known attachment techniques. The inserts can be formed from the same material as the elongate body 306 or from a different material.

In use, an incision can be formed in proximity to an area of bone 310 to which a piece of soft tissue 342 is to be approximated. The suture anchor 300 can then be passed through the incision, for example via a minimally-invasive surgical access device, and implanted in the bone 310. A bore-hole can be drilled in the bone 310 and the suture anchor 300 can be threaded or press-fit therein, or the suture anchor 300 can be self-drilled or self-tapped directly into unprepared bone 310.

The suture anchor 300 can be pre-loaded with a suture 304 before the suture anchor is implanted in bone. Alternatively, the suture 304 can be threaded through the anchor 300 after implantation, for example using a common shuttle maneuver. In either case, as shown in FIGS. 7 and 8, the two free ends 344, 346 of a length of suture 304 can be brought together such that the suture forms an open loop 348. Soft tissue 342 can be captured in the looped portion 348 of the suture 304 as shown, or the suture can be threaded through the soft tissue, e.g., using a suture needle. The two free ends 344, 346 of the suture 304 can be threaded through the first proximal aperture 312 in the head 308 of the suture anchor 300, down along the first channel 364 and its respective first series of cleats 358, through the distal open-end slot 320, up along the second channel 366 and its respective second series of cleats 360, and through the second proximal aperture 314 in the head.

Once the suture anchor 300 is implanted in bone 310 and the suture 304 is threaded therethrough, the surgeon can apply tension to the two free ends 344, 346 of the suture. This can cause the projections of the first and second series of cleats 358, 360 to deflect inwardly towards the sidewalls of the channels 364, 366, such that the suture 304 is free to slide counterclockwise (as viewed from a perspective to the right of that shown in FIG. 7 or to the left of that shown in FIG. 8). In other words, the suture 304 is free to slide distally along the smooth ramped surfaces of the first series of cleats 358 and proximally along the smooth ramped surfaces of the second series of cleats 360. As the free ends 344, 346 of the suture 304 are pulled, the suture slides counterclockwise through the suture anchor 300, drawing the piece of soft tissue 342 at the looped end 348 of the suture into approximation with the bone surface 310. When tension is released from the two free ends 344, 346 of the suture 304, the natural tension of the soft tissue 342 applies a pulling force to the suture in a clockwise direction (as viewed from a perspective to the right of that shown in FIG. 7 or to the left of that shown in FIG. 8). This can cause the sharp ends of the projections of the first and second series of cleats 358, 360 to deflect outwards from the channel sidewalls and to pinch down on the suture 304. The force applied to the suture 304 resists or prevents the suture from slipping in the clockwise direction.

It will thus be appreciated that the soft tissue 342 can be quickly and easily approximated to the bone surface 310, without the need to ever tie off the two free ends 344, 346 of the suture 304 in a knot. After the soft tissue 342 is approximated as desired, the two free ends 344, 346 of the suture 304 can be trimmed and the incision can be closed.

While a single pair of channels 364, 366 and corresponding cleat sets 358, 360 is shown in the illustrated suture anchor 300, it will be appreciated that the suture anchor can also include multiple such pairs. For example, the suture anchor can also include third and fourth channels, with third and fourth series of cleats, formed on the elongate body 306 offset 90 degrees from the first and second channels 364, 366, respectively, and a second suture can be threaded through the suture anchor 300 and engaged by the third and fourth series of cleats. Alternatively, or in addition, more than one series of cleats can be provided in each individual channel. For example, each channel 364, 366 can include a first series of cleats extending from one sidewall of the channel and a second series of cleats extending from the opposite sidewall of the channel. In such embodiments, the two series of cleats in each channel can extend in the same direction (i.e., proximally or distally), such that the suture is free to slide in a first direction across the smooth ramped surfaces of the cleats. When the suture is pulled in a second opposite direction, however, the suture can be pinched between the sharp tips of the opposing cleats, thereby resisting or preventing the suture from sliding in the second opposite direction. The opposing cleats can be positioned directly opposite one another (i.e., at the same longitudinal position along the suture anchor), or can be positioned offset from one another such that they are staggered in an alternating fashion along the length of the suture anchor.

The suture anchors disclosed herein can be formed from any of a variety of materials. In some embodiments, the suture anchors can be formed from a biocompatible, bioabsorbable material which can reduce immunological problems associated with having a foreign substance within the body over a prolonged period of time. Exemplary materials from which the suture anchors disclosed herein can be formed include bioabsorbable elastomers, copolymer combinations such as polylactic acid-polyglycolic acid (PLA-PGA), and bioabsorbable polymers such as aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. In some embodiments, the suture anchors can be formed from polylactic acid, or a composite blend of tricalcium phosphate and polylactic acid. The suture anchors disclosed herein can also be formed from non-absorbable materials, such as polysulfone, or metals such as titanium. The suture-engaging element(s) and/or the cleat inserts can be formed from any of the materials listed above, including titanium.

The suture anchors disclosed herein can be provided in any of a variety of sizes, depending on patient anatomy, procedure type, suture size, and various other parameters which will be readily apparent to one having ordinary skill in the art. In some embodiments, the suture anchors disclosed herein can be between about 1 mm and about 12 mm in diameter and between about 2 mm and about 24 mm in length.

In some embodiments, a kit can be provided that includes one or more of the suture anchors disclosed herein along with one or more sutures for use therewith. For example, an exemplary kit can include a plurality of suture anchors of varying type and size, such that a surgeon can select the appropriate suture anchor for a particular application. The kit can also include a plurality of sutures of various diameters, lengths, colors, materials, and so forth.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components (e.g., sutures) with which the devices will be used, and the methods and procedures in which the devices will be used. The figures provided herein are not necessarily to scale. Although the devices and methods disclosed herein are generally directed to surgical techniques, they can also be used in applications outside of the surgical field.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A suture anchor, comprising:
an elongate body having proximal and distal ends, an inner cavity formed therein, and first and second elongate cut-outs formed in opposed sides of the elongate body;
a suture-engaging element disposed within the inner cavity of the elongate body and having a width that is greater than an outer diameter of the elongate body such that opposed terminal ends of the suture-engaging element protrude radially outward through the first and second elongate cut-outs formed in the elongate body, the suture-engaging element being configured to allow a suture to extend around the elongate body and along the cut-outs and to concurrently allow the suture to slide freely in a first direction and to prevent sliding movement of the suture in a second, opposite direction.

2. The suture anchor of claim 1, wherein the suture-engaging element is retained within the inner cavity of the elongate body.

3. The suture anchor of claim 1, wherein the suture-engaging element is at least one of rotatable about a fixed axis within the inner cavity of the elongate body and flexible about a fixed axis within the inner cavity of the elongate body.

4. The suture anchor of claim 1, wherein a first terminal end of the suture-engaging element is angled proximally toward the proximal end of the elongate body, and a second terminal end of the suture-engaging element is angled distally toward the distal end of the elongate body.

5. The suture anchor of claim 1, wherein the elongate body is substantially cylindrical.

6. The suture anchor of claim 1, wherein the elongate body includes one or more bone-engaging features formed on an exterior surface thereof.

7. The suture anchor of claim 1, wherein the suture-engaging element comprises a central body portion having first and second arms extending tangentially therefrom in opposite directions.

8. The suture anchor of claim 1, wherein the suture-engaging element comprises a central body portion having first and second arms extending therefrom, the first and second arms having respective first and second elbows formed therein.

9. The suture anchor of claim 1, wherein, when the suture anchor is implanted in a bone, tension applied to the suture in the second, opposite direction is effective to force the suture-engaging element into engagement with the bone.

10. A suture anchor, comprising:
an elongate body having proximal and distal ends, an inner cavity formed therein, and first and second elongate cut-outs formed in opposed sides of the elongate body; and
a suture-engaging element with a first arm and a second arm extending laterally therefrom and having a width that is greater than an outer diameter of the elongate body, the suture-engaging element being rotatable about a fixed axis within the inner cavity, the first arm being angled proximally toward the proximal end of the elongate body and the second arm being angled distally toward the distal end of the elongate body, the suture-engaging element being configured such that the first and second arms simultaneously rotate into engagement with a suture when the suture is pulled in a first direction and rotate out of engagement with the suture when the suture is pulled in a second, opposite direction.

11. The suture anchor of claim 10, wherein the suture-engaging element is retained within the inner cavity of the elongate body.

12. The suture anchor of claim 10, wherein the elongate body is substantially cylindrical.

13. The suture anchor of claim 10, wherein the elongate body includes one or more bone-engaging features formed on an exterior surface thereof.

14. The suture anchor of claim 10, wherein the first and second arms have respective first and second elbows formed therein.

15. The suture anchor of claim 10, wherein, when the suture anchor is implanted in a bone, tension applied to the suture in the second, opposite direction is effective to force the suture-engaging element into engagement with the bone.

* * * * *